United States Patent [19]

Goodwin

[11] Patent Number: 5,687,743
[45] Date of Patent: Nov. 18, 1997

[54] HEAD STRAP ASSEMBLY FOR REDUCING SNORING ACTIVITY

[76] Inventor: Isabell Goodwin, 1316 Lakeview Ave., #104, Pueblo, Colo. 81004

[21] Appl. No.: 736,497

[22] Filed: Oct. 24, 1996

[51] Int. Cl.⁶ ............................................. A61F 5/56
[52] U.S. Cl. .................. 128/848; 128/876; 602/18; 602/902
[58] Field of Search ..................... 128/846, 848, 128/859–862; 602/17, 902

[56] References Cited

U.S. PATENT DOCUMENTS

| | | | |
|---|---|---|---|
| 1,296,946 | 3/1919 | Galiardo | 128/848 |
| 1,339,865 | 5/1920 | Rothenberger | 128/848 |
| 1,990,411 | 2/1935 | Lowry | 128/848 |
| 2,507,617 | 5/1950 | Swendiman | 602/17 |
| 5,361,416 | 11/1994 | Petrie | 602/902 |

*Primary Examiner*—Michael A. Brown
*Attorney, Agent, or Firm*—Flanagan & Flanagan

[57] ABSTRACT

A head strap assembly for reducing snoring activity includes a front strap for extending around a head spaced forwardly of ears and below a chin of a user, a rear strap for extending around the head and rearwardly of the ears and above the chin of the user with the rear strap crossing the front strap between the ears and chin of the user, and a link strap interconnecting the front and rear straps above the ears of the user. The front strap preferably has an upper portion and a lower portion with pairs of adjacent ends for positioning on each side of the head of the user. The assembly may also include an adjustable fastening elements which are attached to the pair of adjacent ends of the upper and lower portions of the front strap for providing overlapping releasable coupling of the adjacent ends of the upper and lower portions of the front strap to one another. The assembly may also include an upper chin pad, a lower chin pad and a head pad. The upper chin pad is slidably mounted to the rear strap for positioning above the chin of the user. The lower chin pad is slidably mounted to the lower portion of the front strap for positioning below the chin of the user. The head pad is slidably mounted to the link strap for positioning on the head of the user.

25 Claims, 2 Drawing Sheets

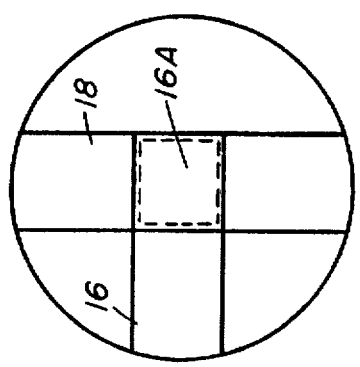
FIG. 5
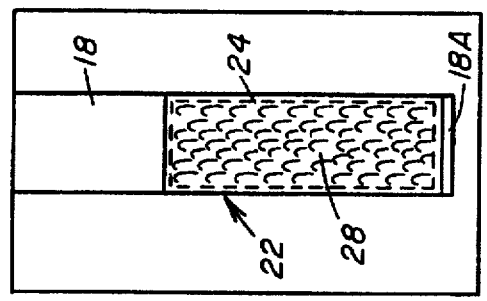
FIG. 4
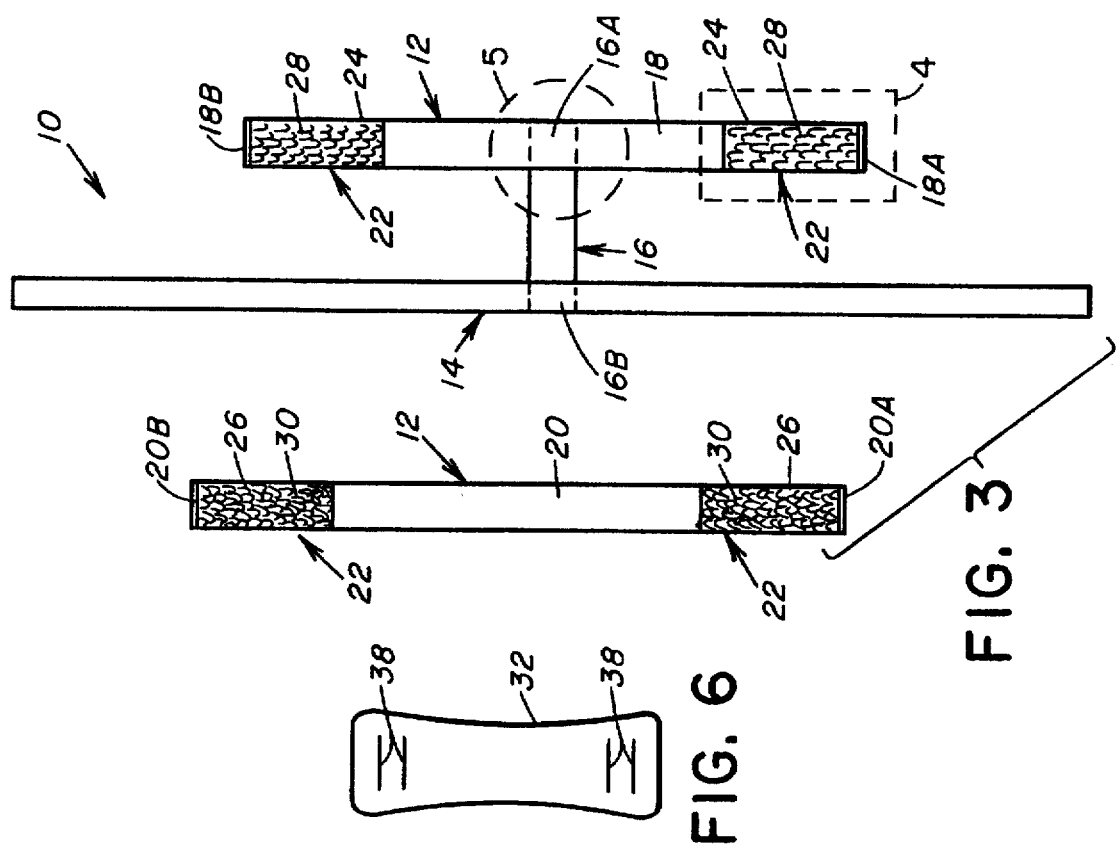
FIG. 3
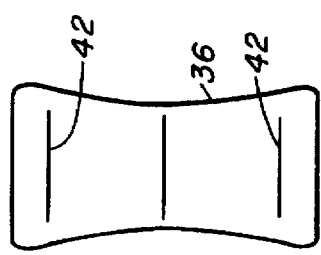
FIG. 6
FIG. 7
FIG. 8

HEAD STRAP ASSEMBLY FOR REDUCING SNORING ACTIVITY

BACKGROUND OF THE INVENTION

1. Field of the Invention

The present invention generally relates to devices for treating sleeping problems and, more particularly, is concerned with a head strap assembly for reducing snoring activity.

2. Description of the Prior Art

For two or more people sleeping in close quarters, snoring can be loathsome to the one or more persons kept awake by it, replacing the best of dreams with the worst of nightmares. Little is more tormenting to others than hearing the obnoxious breathing racket of a snorer sound asleep without regard for anyone else in the same bed or room. Solutions have included throwing any of a variety of objects at or kicking or nudging or cursing the snorer until he or she ceases and desists. Problems exist with these actions in that they may bring about the end to an otherwise rewarding friendship or marriage and/or result in injury to the snorer. Various devices have therefore been developed over the years to provide a more workable solution to the snoring problem.

A more recent one of these prior art devices is disclosed in U.S. Pat. No. 5,361,416 to Petrie et al. The Petrie et al device is an assembly of a cover for the head and a cup for the chin of a user. The head cover and chin cup operate together to maintain the mouth of the user in a closed position and treat sleep apnea by forcing the user to breathe only through his or her nose. The head cover and chin cup both utilize sets of straps and D-rings. The set of straps which are attached to the head cover engage the set of D-rings on the chin cup whereas the set of straps which are attached to the chin cup engage the set of D-rings on the head cover. While the Petrie et al. assembly may function satisfactorily in use, it does not seem to provide a particularly comfortable solution for the problem at hand.

Consequently, a need still exists for a comfortable and yet effective device which provides a solution to the aforementioned problem in the prior art without creating any new problems in place thereof.

SUMMARY OF THE INVENTION

The present invention provides a head strap assembly which is designed to satisfy the aforementioned need for reducing snoring activity. The head strap assembly of the present invention is comfortable and yet effective in operation. The head strap assembly does not utilize any metal fasteners nor a head cover which can be cumbersome to the user. The head strap assembly instead utilizes a plurality of straps to hold the mouth of the user shut with greater comfort and with at least the same level of effectiveness as provided by devices of the prior art.

Accordingly, the present invention is directed to a head strap assembly which comprises: (a) a front strap for extending around a head of a user spaced forwardly of the ears from over a top of the head to below a chin of the user; (b) a rear strap for extending around the head of the user rearwardly of the ears from over the top of the head spaced rearwardly from the front strap to above the chin of the user spaced above the front strap, the rear strap crossing the front strap between the ears and chin of the user; and (c) a link strap interconnecting the front and rear straps above the ears of the user. The front strap preferably has an upper portion and a lower portion with pairs of adjacent ends for positioning on each side of the head of the user.

The head strap assembly preferably further comprises an adjustable fastening means attached to each of the pair of adjacent ends of the upper and lower portions of the front strap for providing overlapping releasable coupling of the adjacent ends of the upper and lower portions of the front strap to one another. The adjustable fastening means are complementary patches of mateable hook and loop fastening elements disposed on opposite surfaces of the adjacent ends of the upper and lower portions of the front strap and facing one another for making contact with one another.

The head strap assembly preferably further comprise an upper chin pad, a lower chin pad and a head pad. The upper chin pad is slidably mounted to the rear strap for positioning above the chin of the user. The upper chin pad has at least a pair of spaced apart opposite slits for receiving the rear strap therethrough. The lower chin pad is slidably mounted to the lower portion of the front strap for positioning below the chin of the user. The lower chin pad has at least a pair of spaced apart opposite slits for receiving the lower portion of the front strap therethrough. The head pad is slidably mounted to the link strap for positioning on the head of the user. The head pad has at least a pair of spaced apart opposite slits for receiving the link strap therethrough.

The arrangement of the head strap assembly about the chin and head of the user is intended to hold the mouth of the user shut and to thereby reduce the level of snoring activity of the user. At the same time, more oxygen is delivered to the lungs of the user because the user will be breathing primarily through the nose. The front strap is forward of the ears of the user in order to make the greatest use of the direct pull upward on the chin to close the mouth of the user. The rear strap goes behind the ears of the user in order to provide an up and back pull to the assembly and thereby hold the chin to the upper jaw of the user.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 3 is a layout of the front, rear and link straps of the head strap assembly.

FIG. 4 is a detailed view of the area of the head strap assembly enclosed by rectangle 4 of FIG. 3.

FIG. 5 is a detailed view of the area of the head strap assembly enclosed by circle 5 of FIG. 3.

FIG. 6 is an enlarged plan view of an upper chin pad of the head strap assembly.

FIG. 7 is an enlarged plan view of a lower chin pad of the head strap assembly.

FIG. 8 is an enlarged plan view of a head pad of the head strap assembly.

DETAILED DESCRIPTION OF THE INVENTION

Figure 1:
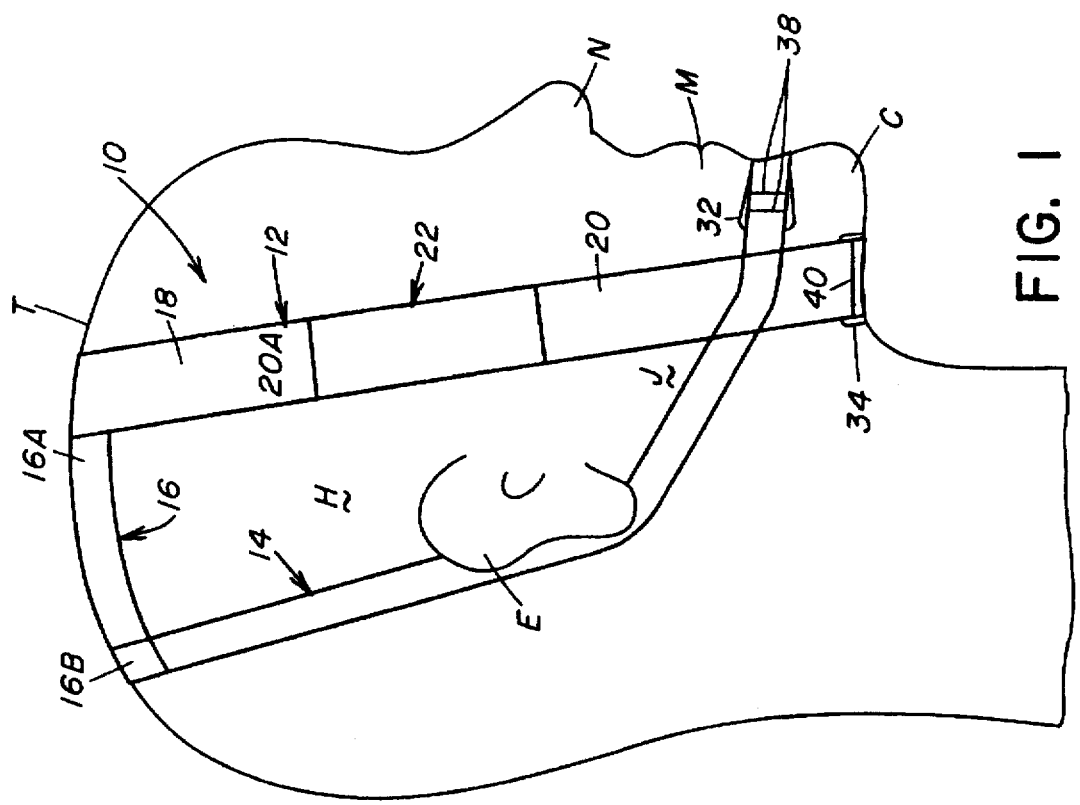
FIG. 1 is a side elevational view of a head strap assembly of the present invention deployed on the head of a user.
Figure 2:
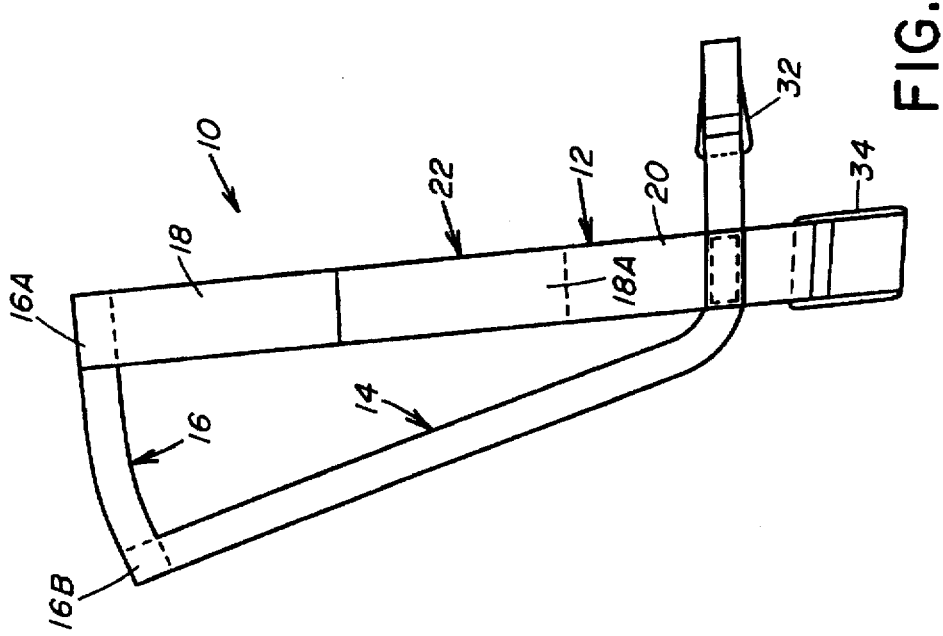
FIG. 2 is a side elevational view of the head strap assembly removed from the head of a user.

Referring to the drawings and particularly to FIGS. 1 to 3, there is illustrated a head strap assembly, generally designated 10, of the present invention for reducing snoring activity. Basically, the head strap assembly 10 includes a front strap 12, a rear strap 14 and a link strap 16. The front strap 12 is adapted for extending around a head H of a user spaced forwardly of the ears E from over a top T of the head H to below a chin C of the user. The rear strap 14 is adapted for extending around the head H of the user rearwardly of the ears E from over the top T of the head H spaced rearwardly from the front strap 12 to above the chin C of the user spaced above the front strap 12. The rear strap 14 crosses the front strap 12 between the ears E and chin C of the user. The link strap 16 extends between and interconnects the front and rear straps 12, 14 above the ears E of the user, particularly along the top T of the head H of the user. The front, rear and link straps 12, 14, 16 are comprised of substantially elastic material and have substantially rectangular configurations.

Referring now to FIGS. 1 to 4, the front strap 12 has an upper portion 18 and a lower portion 20 with pairs of adjacent ends 18A, 18B and 20A, 20B for positioning on each side of the head H of the user forward of the ears E. As one example, the upper portion 18 generally has a width of one inch and a length of 13.50 inches, but can have any other suitable size. The lower portion 20 generally has a width of one inch and a length of 14.25 inches, but can have any other suitable size. The rear strap 14 generally has a width of 0.50 inches and a length of 23.75 inches, but can have any other suitable size. The link strap 16 generally has a width of one inch and a length of 2.50 inches, but can have any other suitable size. Also, the link strap 16 has a pair of opposite ends 16A, 16B which are stitched to an intermediate location on the upper portion 18 of the front strap 12 and to an intermediate location on the rear strap 14 so that the link strap 16 can be positioned along the top T of the head H of the user. The link strap 16 may also be attached to the front and rear straps 12, 14 by any other suitable means and at any other suitable location thereon for positioning at any other suitable location on the head H of the user. It can be readily observed in FIG. 3 that the link strap 16 is substantially shorter in length than either of the lengths that the opposite ends 18A, 18B of the upper portion 18 of the front strap 12 extend from the link strap 16.

The head strap assembly 10 preferably further includes an adjustable fastening means 22 which is attached to each of the pair of adjacent ends 18A, 18B and 20A, 20B of the upper and lower portions 18, 20 of the front strap 12. The adjustable fastening means 22 is adapted for providing overlapping releasable coupling of the adjacent ends 18A, 18B and 20A, 20B of the upper and lower portions 18, 20 of the front strap 12 to one another. Preferably, the adjustable fastening means 22 are complementary patches 24, 26 of mateable hook and loop fastening elements 28, 30 disposed on opposite surfaces of the adjacent ends 18A, 18B and 20A, 20B of the upper and lower portions 18, 20 of the front strap 12 and facing one another for making contact with one another. The patches 24, 26 generally have a substantially rectangular configuration with a width equal to the width of the upper and lower portions 18, 20 of the front strap 12 and a length of three inches, but can have any other suitable size and shape. The patches 24, 26 are stitched to the adjacent ends 18A, 18B and 20A, 20B of the upper and lower portions 18, 20 of the front strap 12, but can be attached by any other suitable means. The patches 24 of mateable hook fastening elements 28 are preferably sewn to an outside-facing surface of the adjacent ends 18A, 18B of the upper portion 18 of the front strap 12 while the patches 26 of the mateable loop fastening elements 30 are preferably sewn to an inside-facing surface of the adjacent ends 20A, 20B of the lower portion 20 of the front strap 12 such that the patches 24, 26 are facing one another for making contact with one another. The patches 24, 26 can also have any other suitable arrangement with regard to one another.

Referring now to FIGS. 1, 2, 6 to 8, the head strap assembly 10 preferably further includes an upper chin pad 32, a lower chin pad 34 and a head pad 36. Each of the pads 32, 34, 36 is preferably made from a neoprene material or the like which provides a cushion for the front, rear and link straps 12, 14, 16 contacting the chin C and/or head H of the user. The upper chin pad 32 is slidably mounted onto the rear strap 14 for positioning above the chin C of the user and has a substantially hourglass configuration, but can have any other suitable shape. The upper chin pad 32 has at least a pair of spaced apart opposite slits 38 and preferably has two pairs of spaced apart opposite slits 38 for receiving the rear strap 14 therethrough. The lower chin pad 34 is slidably mounted onto the lower portion 20 of the front strap 12 for positioning below the chin C of the user and has a substantially rectangular configuration, but can have any other suitable shape. The lower chin pad 34 has at least a pair of spaced apart opposite slits 40 and preferably has two pairs of spaced apart opposite slits 40 for receiving the lower portion 20 of the front strap 12 therethrough. The head pad 36 is slidably mounted to the link strap 16 for positioning on the head of the user and has a substantially hourglass configuration, but can have any other suitable shape. The head pad 36 has at least a pair and preferably only a pair of spaced apart opposite slits 42 for receiving the link strap 16 therethrough.

As one example, the upper chin pad 32 generally has a width of 0.75 inches at the waist and a width of one inch at ends thereof and a of three inches. The slits 38 generally have a distance between them of 2.50 inches and are about 0.50 inches in length. The lower chin pad 34 generally has a width of 1.25 inches and a length of 3.50 inches. The pairs of slits 40 generally have a distance between them of 2.50 and three inches and are about one inch in length. The head pad 36 generally has a width of 1.25 inches at the waist and a width of 1.63 inches at ends thereof and a length of three inches. The slits 42 generally have a distance between them of 2.25 inches and are about one inch in length.

The arrangement of the head strap assembly 10 about the chin C and head H of the user is intended to hold the mouth M of the user shut and to thereby reduce the level of snoring activity of the user. At the same time, more oxygen is delivered to the lungs of the user because the user will be breathing primarily through the nose N. The front strap 12 is forward of the ears E of the user in order to make the greatest use of the direct pull upward on the chin C to close the mouth M of the user. The rear strap 14 goes behind the ears E of the user in order to provide an up and back pull to the head strap assembly 10 and thereby hold the chin C toward the upper jaw J of the user.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. A head strap assembly for reducing snoring activity, said assembly comprising:
    (a) a front strap for extending around a head of a user spaced forwardly of ears of the user from a first location over a top of the head downwardly to below a chin of the user;

(b) a rear strap for extending around the head of the user rearwardly of the ears from a second location over the top of the head spaced a short distance rearwardly from said front strap so as to be above the ears of the user downwardly to above the chin of the user spaced above said front strap, said rear strap crossing said front strap between the ears and chin of the user; and (c) a link strap interconnecting said front and rear straps and being spaced above the ears of the user and disposed on the top of the head of the user, said link strap having front and rear opposite ends attached respectively to said front and rear straps;

(d) said front strap including (i) an upper portion having a pair of opposite ends and attached at a location between said opposite ends to said front end of said link strap, said opposite ends of said upper portion of said front strap extending in opposite directions away from said front end of said link strap and downwardly toward the chin of the user, (ii) a lower portion separate from said upper portion of said front strap, said lower portion adapted to extend under and around the chin of the user and having a pair of opposite ends extending upwardly from the chin for meeting and overlapping with the downwardly extending opposite ends of the upper portion of the front strap on opposite sides of the head of the user forwardly of the ears, and (iii) adjustable fastening means attached to each of said pairs of opposite ends of said upper and lower portions of said front strap for providing overlapping releasable coupling of said pair of opposite ends of said upper portion of said front strap to said pair of opposite ends of said lower portion of said front strap on opposite sides of the head of the user forwardly of the ears, said link strap being substantially shorter in length than either lengths that said opposite ends of said upper portion of said front strap extend in opposite directions from said link strap.

2. The assembly of claim 1 wherein said front, rear and link straps are comprised of a substantially elastic material.

3. The assembly of claim 1 wherein said front, rear and link straps have substantially rectangular configurations.

4. The assembly of claim 1 further comprising:

(e) an upper chin pad slidably mounted to said rear strap for positioning above the chin of the user.

5. The assembly of claim 4 wherein said upper chin pad has a substantially hourglass configuration.

6. The assembly of claim 4 wherein said upper chin pad has at least a pair of spaced apart opposite slits for receiving said rear strap therethrough.

7. The assembly of claim 1 further comprising:

(e) a lower chin pad slidably mounted to said front strap for positioning below the chin of the user.

8. The assembly of claim 7 wherein said lower chin pad has a substantially rectangular configuration.

9. The assembly of claim 7 wherein said lower chin pad has at least a pair of spaced apart opposite slits for receiving said front strap therethrough.

10. The assembly of claim 1 further comprising:

(e) a head pad slidably mounted to said link strap for positioning on the head of the user.

11. The assembly of claim 10 wherein said head pad has a substantially hourglass configuration.

12. The assembly of claim 10 wherein said head pad has at least a pair of spaced apart opposite slits for receiving said link strap therethrough.

13. The assembly of claim 1 wherein each of said adjustable fastening means are complementary patches of mateable hook and loop fastening elements disposed on opposite surfaces of said adjacent ends of said upper and lower portions of said front strap and facing one another for making contact with one another.

14. A head strap assembly for reducing snoring activity, said assembly comprising:

(a) a front strap for extending around a head of a user spaced forwardly of ears and below a chin of the user, said front strap having an upper portion and a lower portion separate from said upper portion, said upper portion having a pair of opposite ends and said lower portion having a pair of opposite ends for positioning adjacent to said opposite ends of said upper portion on opposite sides of the head of the user forwardly of the ears;

(b) an adjustable fastening means attached to each of said pair of opposite ends of said upper and lower portions of said front strap for providing overlapping releasable coupling of said opposite ends of said upper portion to said opposite ends of said lower portion when disposed adjacent to one another on the opposite sides of the head of the user forwardly of the ears, said adjustable fastening means being complementary patches of mateable hook and loop fastening elements disposed on facing surfaces of said opposite ends of said upper and lower portions of said front strap for making releasable contact with one another;

(c) a rear strap for extending around the head rearwardly of the ears and above the chin of the user, said rear strap crossing said front strap between the ears and chin of the user; and (d) a link strap interconnecting said front and rear straps above the ears of the user.

15. The assembly of claim 14 wherein said front, rear and link straps are comprised of a substantially elastic material.

16. The assembly of claim 14 wherein said front, rear and link straps have substantially rectangular configurations.

17. The assembly of claim 14 further comprising:

(e) an upper chin pad slidably mounted to said rear strap for positioning above the chin of the user.

18. The assembly of claim 17 wherein said upper chin pad has a substantially hourglass configuration.

19. The assembly of claim 17 wherein said upper chin pad has at least a pair of spaced apart opposite slits for receiving said rear strap therethrough.

20. The assembly of claim 14 further comprising:

(e) a lower chin pad slidably mounted to said lower portion of said front strap for positioning below the chin of the user.

21. The assembly of claim 20 wherein said lower chin pad has a substantially rectangular configuration.

22. The assembly of claim 20 wherein said lower chin pad has at least a pair of spaced apart opposite slits for receiving said lower portion of said front strap therethrough.

23. The assembly of claim 14 further comprising:

(e) a head pad slidably mounted to said link strap for positioning on the head of the user.

24. The assembly of claim 23 wherein said head pad has a substantially hourglass configuration.

25. The assembly of claim 23 wherein said head pad has at least a pair of spaced apart opposite slits for receiving said link strap therethrough.

* * * * *